Figure 1:
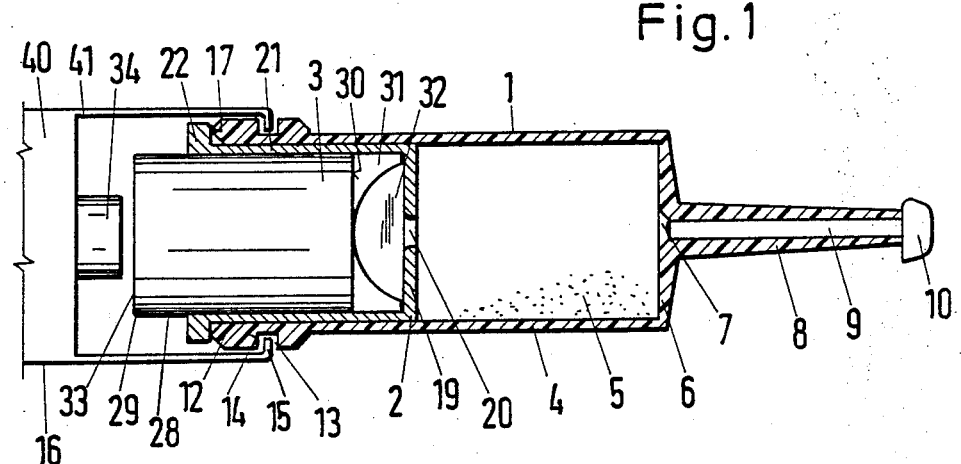

United States Patent [19]
Mühlbauer

[11] Patent Number: 4,941,751
[45] Date of Patent: Jul. 17, 1990

[54] MULTI-COMPONENT MIXING CAPSULE HAVING AN EJECTION DEVICE FOR THE MIXED COMPOUND, IN PARTICULAR FOR DENTAL PURPOSES

[76] Inventor: Ernst Mühlbauer, Elbgaustr. 248, 2000 Hamburg 53, Fed. Rep. of Germany

[21] Appl. No.: 379,862

[22] Filed: Jul. 14, 1989

[30] Foreign Application Priority Data

Jul. 18, 1988 [DE] Fed. Rep. of Germany ... 8809184[U]

[51] Int. Cl.$^5$ .............................................. B01F 5/06
[52] U.S. Cl. .................................. 366/176; 366/602; 366/184; 206/219; 206/63.5
[58] Field of Search .................. 366/602, 76, 176, 184; 206/219, 63.5

[56] References Cited

U.S. PATENT DOCUMENTS

| | | | |
|---|---|---|---|
| 2,487,236 | 11/1949 | Greenberg | 366/602 X |
| 3,595,439 | 7/1971 | Newby | 206/219 X |
| 3,684,136 | 8/1972 | Baumann | 206/219 X |
| 3,731,853 | 5/1973 | Baumann et al. | 206/219 X |
| 3,739,947 | 6/1973 | Baumann et al. | 206/219 X |
| 3,762,540 | 10/1973 | Baumann et al. | 206/219 |
| 3,831,742 | 8/1974 | Gardella et al. | 206/219 |
| 4,136,775 | 1/1979 | Zaltsman | 366/602 X |

FOREIGN PATENT DOCUMENTS 1939316  8/1973  Fed. Rep. of Germany .
3718326 12/1988  Fed. Rep. of Germany .

Primary Examiner—Frankie L. Stinson
Attorney, Agent, or Firm—Chilton, Alix & Van Kirk

[57] ABSTRACT

Multi-component mixing capsule having an ejection device, in particular for dental purposes. A receptacle part (1) forming a mixing chamber (5) contains a piston (2) which for its part comprises an accommodation chamber (31) for a film container (32) and a ram (3). To enable the ram (3) to be pushed forward inside the piston (2) in order to transfer the film container contents into the mixing chamber (5) without the piston (2) being displaced in the receptacle part (1), the piston (2) is provided on a portion protruding rearwards beyond the receptacle part (1) with a radial projection which is supported on the tool or on the rearward end face (17) of the receptacle part (1). Support ends as soon as the ram (3) has travelled the necessary distance in the piston (2) to empty the film container (32). For this purpose, the projection (22) may have the ability to be torn off from the piston or bent inwards.

4 Claims, 2 Drawing Sheets

MULTI-COMPONENT MIXING CAPSULE HAVING AN EJECTION DEVICE FOR THE MIXED COMPOUND, IN PARTICULAR FOR DENTAL PURPOSES

The invention relates to a mixing capsule having an ejection device for a plastic compound, in particular for dental purposes, having a receptacle part forming a mixing chamber with an ejection opening, having a piston which can be displaced in the receptacle part and comprises a perforated wall limiting the mixing chamber at its end facing away from the ejection opening and, on the other side of the perforated wall, an accommodation chamber for a film container containing a liquid component, and having a ram which can be displaced in the accommodation chamber by means of a tool in order to empty the film container into the mixing chamber, it being possible for the piston to be supported directly or indirectly on the tool against the tool force displacing the ram.

A known mixing capsule of this type (DE-C 1 39,316, FIG. 4 A) has, within the cylindrical receptacle part, a pot-shaped piston whose wall protrudes beyond the receptacle part at the rear and can be provided with a bayonet ring which is supported on the rear end face of the receptacle part. When, for the purpose of emptying the film container into the mixing chamber, the ram situated within the pot-shaped piston is acted upon by a tool which, on the one hand, presses against the ram and, on the other hand, supports the receptacle part at its ejection end, the bayonet ring transmits the force exerted on the piston to the receptacle part, with the result that the piston maintains its rest position. The mixing capsule is then inserted into one of the customary vibration mixers in order to mix the components brought together in the mixing chamber and prepare them for application. The bayonet ring is then released and the capsule is inserted once again into the tool in order to eject the chamber contents. - The known capsule is not very practical because the elements provided for mutual connection on the piston and bayonet ring are expensive to produce and, because of the large forces to be transmitted, require the use of high-grade materials. In addition, the release of the small bayonet ring from the capsule is troublesome unless it fits so loosely that it could be released unintentionally, thereby giving rise to the risk of an incomplete transfer of the liquid components into the mixing chamber.

In another known mixing capsule (DE-C 1,939,316, FIG. 1 A.), the mixing chamber wall has, upstream of the piston, a circumferencial bead which constricts the path of the piston at this point and offers the displacement of the piston such resistance that a sufficient force for the destruction and emptying of the film container into the mixing chamber, can be produced. However, because the resistance cannot be accurately defined with these means, it must be made so considerably higher than the force required for the destruction and emptying of the film container that it seriously impedes the ejection process. In addition, the known arrangement has the disadvantage that, during ejection, the piston cannot come to rest leak-proofly against the mixing chamber wall as it slides past the bead.

In another, different mixing capsule (DE-A 3,718,326), which does not belong to the prior art, these disadvantages are avoided by the fact that the elements of the tool which serve to hold the piston fast in its rest position during the emptying of the film container into the mixing chamber act on the piston through the wall of the receptacle part.

The object on which the invention is based is to create a mixing capsule of the type mentioned at the outset in which the piston is held securely in its rest position during the emptying of the film container without the expenditure involved in production and use thereby being increased or a considerable resistance having to be overcome during the ejection of the compound.

The solution according to the invention consists in the fact that a portion of the piston which, in the rest condition, protrudes beyond the rearward end of the receptacle part, which end is remote from the ejection opening, has a radial projection forming a supporting face.

This projection can be provided for indirect cooperation with the tool. For the purpose of activation, i.e. for the purpose of transferring the liquid component into the mixing chamber, the capsule is then inserted into the tool in such a way that its supporting arrangements cooperate only with the piston. After activation and mixing, the capsule is inserted into the tool once again, in particular in a position such that the supporting arrangements of the tool cooperate with the receptacle part and the piston is thus free for a movement directed into the mixing chamber.

However, those embodiments of the invention are preferred in which the supporting arrangements of the tool cooperate exclusively with the receptacle part because the risk of incorrect operation is thereby excluded. For this, the projection on the piston is designed such that it is supported on the receptacle part, while the receptacle part is designed to cooperate with the tool. Lateral projections which cooperate with the supporting arrangements of the tool can be provided for this on the receptacle part.

Since the projection of the piston, which projection cooperates with the receptacle part, is only intended to hold the piston in its rest position during the activation of the mixing capsule, whereas, after mixing, the piston should be displaceable with as little resistance as possible, according to a special feature of the invention the projection of the piston is, after a limited advance of the ram, self-releasing. This means that the blocking function of the projection is tied to a limited portion of the advance of the ram which is sufficient to empty the film container, while it ends after this.

In a particularly advantageous embodiment of the invention, this principle is realised by the projection being connected to the perforated wall of the piston via a tearable portion, the tear strength of which is greater than the ram force required to empty the film container. For example, the projection, which is preferably designed as a circumferential annular flange, can be connected to the perforated wall of the piston via one or more thin material bridges which tear away when a certain force threshold sufficiently higher than the force required to empty the film container, is exceeded. As a result, the resistance against the pushing forward of the piston ends and no additional resistance has to be overcome during the ejection of the contents of the mixing chamber. Since the cross-sections of the material bridges can be very accurately dimensioned, the force threshold can also be very accurately determined.

In another embodiment of the invention the projection is held against a radially flexible portion of the piston and is held in its position supported on the receptacle part by a face of the ram which, in the rest position, protrudes rearwards beyond the projection by about the distance which the ram travels relative to the piston in order to completely empty the film container. As soon as the ram has been pushed so far that the film container is with certainty empty, the radial support of the projection ends, with the result that said projection can give way inwards and loses the supporting contact with the rearward end face of the receptacle part. To ensure that support is possible only after the emptying of the liquid container, it is possible to provide according to the invention that the projection is connected to the perforated wall of the piston via an elastic part and that the release of the projection takes place only after a certain elastic strain of this part. In other words, the distance by which the supporting face of the ram protrudes rearwards beyond the projection is somewhat smaller than the distance it moves out of the rest position into the position after the complete emptying of the film bag.

Figure 2:
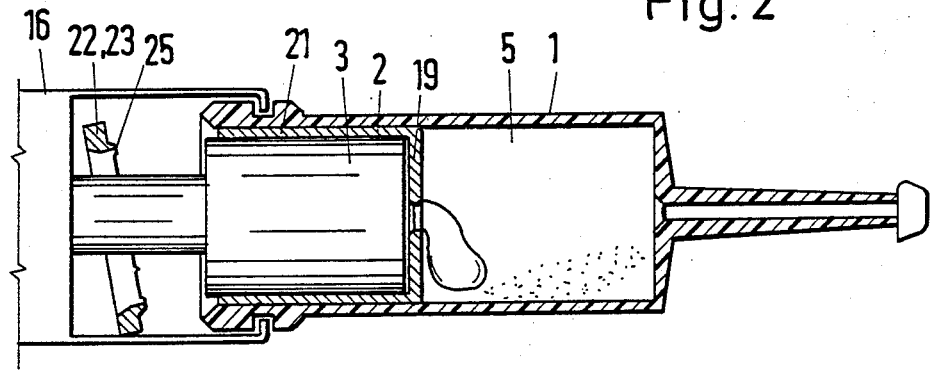
Figure 3:
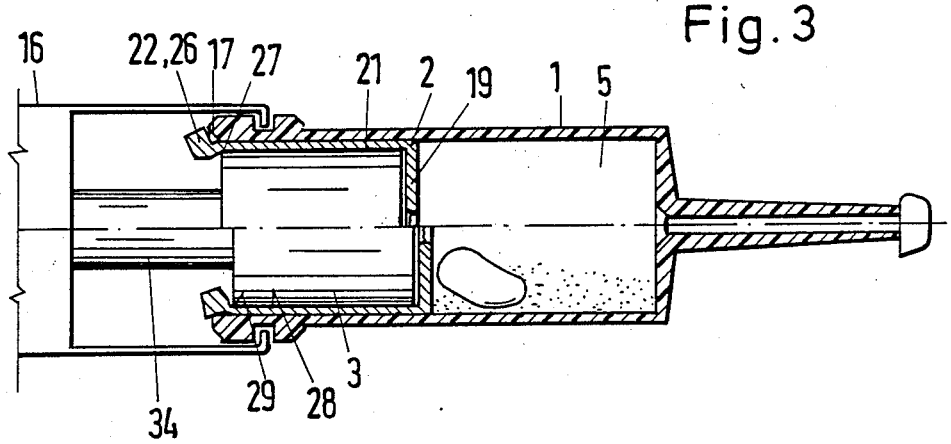
Figure 4:
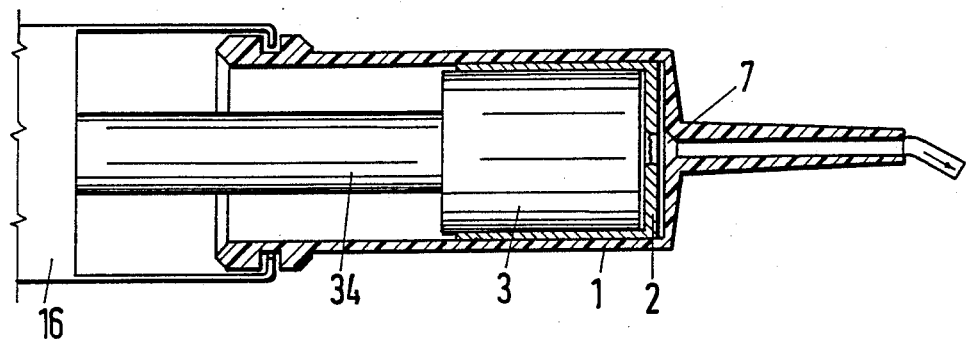
Figure 5:
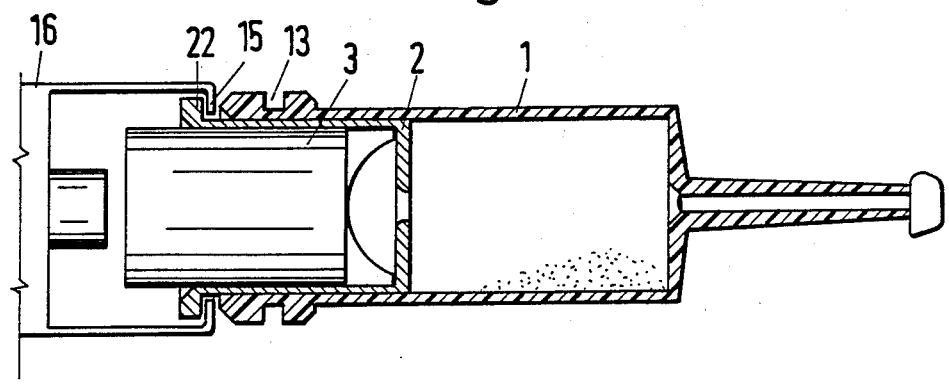
Figure 6:
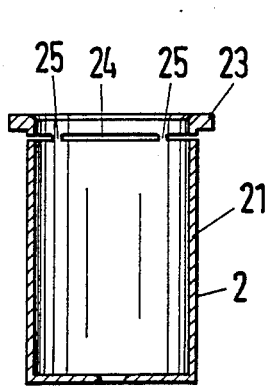
Figure 7:
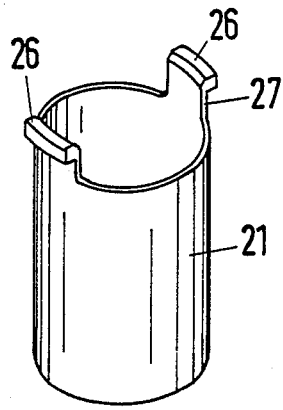
Figure 8:
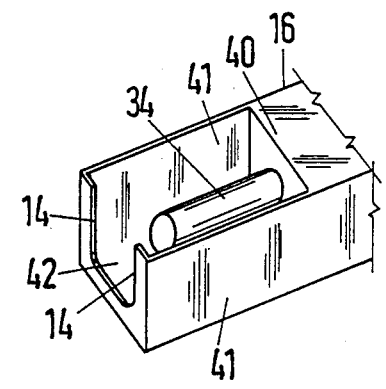

The invention is explained in greater detail below with reference to the drawing and the advantageous exemplary embodiments are illustrated schematically. In the drawing:

FIG. 1 shows a longitudinal section of the capsule in the rest condition,

FIG. 2 shows a representation corresponding to FIG. 1 of a first embodiment, after activation, FIG. 3 shows a representation corresponding to FIG. 2 of another embodiment, FIG. 4 shows the first embodiment in the emptied condition, FIG. 5 shows a third embodiment in the rest condition, FIGS. 6 and 7 show the piston of the first and second embodiment, illustrated separately and FIG. 8 shows a perspective representation of the tool part used for the mixing capsule according to the invention.

The capsule is formed by the receptacle part 1, the piston 2 and the ram 3. Within the cylindrical wall 4, the receptacle part 1 forms the mixing chamber 5 which is limited at the front by an end wall 6 having an ejection opening 7 adjoining which is an ejection channel 8 which, in the rest condition, is sealed by a pin 9 until after mixing, which pin fills it essentially completely up to the mixing chamber and can be pulled off by means of the head 10.

Behind the mixing chamber 5, the cylindrical walls 4 of the receptacle part 1 form an efficiently sealing guide for the piston 2 and have an outer projection 12 which—preferably in the form of a groove 13—forms a forward-facing stop face 14 for cooperating with the claws 15 of a tool 16. The receptacle part 1 ends in a rearward end face 17 which can be bevelled inward to form a circumferential ridge which has a larger diameter than the inner face of the wall 4.

The cylindrical wall 4 accomodates the piston 2 with a tight fit, said piston comprising an end wall 19 which limits the mixing chamber 5 at the rear, runs parallel to the forward end face 6 and has an opening 20, a cylindrical wall 21 which cooperates leak-proofly with the cylinder wall 4 and at the rearward end of the latter, a radial projection 22 which grips behind the rearward end face 17 of the receptacle part. In the first embodiment, the projection 22 is designed as a flange 23 running round in the form of a ring (see FIG. 6) which is separated from the piston wall 21 by a circumferential slot 24 and it is only connected to it by a few, thinly dimensioned material bridges 25.

In the second embodiment (FIG. 7), the projection 22 is in the form of a small number of hooks 26 which are connected via flexible connection pieces 27 to the piston wall 21. It is of course possible for a plurality of such hooks 26 to be provided distributed over the circumference, being separated from one another by gaps, with the result that they can be bent radially inwards without hindering one another.

Within the piston 2 is the ram 3, which has an end face 30 which runs parallel to the rearward face of the perforated wall 19 and with the latter forms a chamber 31 to accommodate a film container 32. By pushing the ram 3 forwards, the chamber 31 can be reduced in size, the film container 32 caused to burst in the region of the opening 20 and the liquid contents of the film bag emptied into the mixing chamber 5. For this purpose, the ram 3 is guided with axial movement in the piston and has a rearward-facing end face 33 for cooperation with the ram 34 of the tool 16. It is evident that the ram 3, which in the figures is represented as a solid cylinder, can be provided with suitable bores or reductions in cross-section for the purpose of decreasing the material. The only things of importance are the end face parallel to the perforated wall 19, the axial guidance in the piston 2, the presence of a rearward end face for cooperation with the tool ram and, in the second embodiment of the invention, a holding face 28 adjacent to the projection 22, 26.

FIG. 8 shows the significant part of the tool, which is known per se. From the tool body 40 there start two essentially parallel walls or arms 41 which end in radially inward-pointing flanges which form the claws 14 which, in accordance with the above explanation, serve to support the capsule. The tool ram 34 can be pushed forwards out of the tool body 40 in the direction of the arrow between the walls or arms 41 in order to actuate the ram 3 of the capsule.

FIGS. 1, 2 and 4 represent the essential functional stages of the first embodiment of the capsule.

The capsule according to FIG. 1, which is in the rest condition, is introduced into the tool in order to be activated. If, starting from the rest condition illustrated in FIG. 1, the ram 3 of the capsule is pushed forwards, a pressure is exerted on the film container 32 which raises the internal pressure of the latter until the container bursts in the region of the opening 20. As the ram is pushed further forward against the perforated wall 29, the volume of the chamber 31 is reduced until the film container has been essentially completely emptied. This procedure presupposes that the piston 2 remains approximately in the illustrated position. For this purpose it is supported by means of the projection 22 on the rearward end face 17 of the receptacle part 1. To ensure that this is possible, the strength of the material bridges 25 is dimensioned such that their tear strength is significantly higher than the force required to empty the film container 32.

Once the ram 3 has reached its forwardmost position in the piston 2, a further advance is only possible by destroying the material bridges 25. The flange 23 forming the projection 22 is broken off by the wall 21 of the piston 2 and lies free behind the capsule in the tool. This is a clearly visible sign that the activation procedure is ended. The capsule, which is removed from the tool, is now inserted into a commercially available vibration mixer for the purpose of mixing the components brought together in the mixing chamber 5. The capsule is then inserted into the tool once again (FIG. 4). By pushing the ram 3 of the piston 2 further, the compound is emptied out from the mixing chamber 5 through the ejection channel 9.

In the second embodiment, the piston 2 can, during the activation phase only be supported on the rearward end face 17 of the receptacle part 1 if the hooks 26 forming the projection 22 are held in their position illustrated in FIG. 1 and FIG. 7. This is achieved by the fact that they are held by the outer face 28 of the ram 3. This possibility ends when the rearward edge 29 of this face has passed the hooks 26, with the result that as indicated in FIG. 3, said hooks can bend back inwards. The further abovementioned ridge of the rearward end face 17 of the receptacle part 1 is from the face 28, the greater is the bending moment which endeavours to tilt the hooks 26 inwards and the easier the effect illustrated in FIG. 3 occurs as soon as the edge 29 has passed the hooks 26. The length of the face 28 is dimensioned such that this occurs only when the forward end face 30 of the ram 3 has, but for the remains of the film container, reached the rearward face of the perforated wall 19 and the wall 21 of the piston 2 and/or the flexible connection pieces 27 have stretched a little. As the ram 3 advances further, the hooks 26 fold completely inwards, as illustrated at the bottom of FIG. 3, with the result that no resistance is offered to the further advance, together, of the ram 3 and the piston 2. In this stage, the activation of the capsule has ended. The components brought together in the mixing chamber 5 can be mixed and then ejected as shown in FIG. 4.

In the third embodiment according to FIG. 5, the projection 22 of the piston 2 is not supported on the rearward end face of the receptacle part 1 during the activation phase but directly on the claws 15 of the tool 16. Only after the mixing of the components is the capsule inserted into the tool 16 in such a way that its claws 15 engage in the groove 13 of the receptacle part 1. Structure and functioning are in other respects identical to those of the other examples.

The invention has, inter alia, the advantage that the leak-proof contact between the piston 2 and the internal face of the receptacle part 1 is in no way jeopardised by structural measures serving to transmit force during the activation phase. It is therefore also possible to use the capsule according to the invention for components which must be sealed off from the atmosphere because, for example, they are hygroscopic, or which are harmful in the unmixed state. In contrast, known capsules used for such substances have in addition to be welded into protective bags. In order to promote the mutual leak-proof contact of the walls 4 and 21, the receptacle part 1 can be composed of elastically yielding material, for example polyethylene, and the piston can have a certain interference relative to the inside diameter of the receptacle part 1. The piston 2, on the other hand, is expediently composed of a harder material to ensure that the complete emptying of the film bag 32 is not jeopardised by an undesired deformation of the perforated wall 19.

Additional means can be provided which indicate the completion of the activation phase, i.e. the complete transfer of the film container contents into the mixing chamber. It is also possible for devices to be provided which prevent an unintended advance of the ram 3 and of the piston 2 after the completion of the activation phase and are removed from the capsule manually only after the removal of the capsule from the tool so that the ejection of the compound from the capsule becomes possible after mixing.

I claim:

1. A capsule usable with an actuating tool, for mixing components and ejecting the resulting mixed compound, comprising:
    a receptacle part (1) having a front portion forming a mixing chamber (5) with an ejection opening (7) in a front wall thereof and an open rear portion;
    a hollow piston (2) which can be displaced in the receptacle part (1), the piston including a rear portion initially extending rearward of the receptacle part and having a radial projection thereon and a perforated front wall (19) defining a rear wall of the mixing chamber (5) away from the ejection opening (7), the hollow portion of the piston on the rear side of the perforated wall defining an accommodation chamber (31) for a film container (32) containing a liquid component;
    a ram (3) which can be displaced in the accommodation chamber (31) by the actuating tool (16) in order to first empty the film container (32) through the perforated front wall (19) into the mixing chamber (5), and then advance the piston relative to the receptacle to eject the mixed compound;
wherein,
    the piston (2) is initially supported relative to the receptacle by the projection against the tool force pushing forward the ram (3), and then is self-released from the receptacle while the tool advances the ram and piston to empty the film container, and
    the projection (22, 23) is connected to the perforated wall (19) of the piston (2) via a tearable portion (25), the tear strength of which is greater than the force of the advancing ram required to empty the film container (32).

2. The capsule according to claim 1, characterized in that the projection (22) is an annular flange (23).

3. A capsule usable with an actuating tool, for mixing components and ejecting the resulting mixed compound comprising:
    a receptacle part (1) having a front portion forming a mixing chamber (5) with an ejection opening (7) in a front wall thereof and an open rear portion;
    a hollow piston (2) which can be displaced in the receptacle part (1), the piston including a rear portion initially extending rearward of the receptacle part and having a radial projection thereon and a perforated front wall (19) defining a rear wall of the mixing chamber (5) away from the ejection opening (7), the hollow portion of the piston on the rear side of the perforated wall defining an accommodation chamber (31) for a film container (32) containing a liquid component;
    a ram (3) which can be displaced in the accommodation chamber (31) by the actuating tool (16) in order to first empty the film container (32) through the perforated front wall (19) into the mixing chamber (5), and then advance the piston relative to the receptacle to eject the mixing compound;
wherein,
    the piston (2) is initially supported relative to the receptacle by the projection against the tool force pushing forward the ram (3), and then is self-released from the receptacle while the tool advances the ram and piston to empty the film container, and the projection (22) is radially flexible and initially held radially outward into engagement with the receptacle part (1) by the ram (3), the ram initially protruding rearwards beyond the projection (22) by about the distance that the ram (3) travels relative to the piston (2) in order to completely empty the film container (32).

4. The capsule according to claim 3, characterized in that the distance by which the ram (3) holding the projection (22) protrudes rearwards beyond the projection (22) is smaller than the distance the ram (3) has to move to empty the film container (33) and in that the projection (22, 26) is connected to the front wall (19) of the piston (2) by an elastic part (21, 27).

* * * * *